US011850004B2

(12) United States Patent
Sorger et al.

(10) Patent No.: US 11,850,004 B2
(45) Date of Patent: Dec. 26, 2023

(54) SYSTEMS AND METHODS FOR DETERMINING AN ARRANGEMENT OF EXPLANTED TISSUE AND FOR DISPLAYING TISSUE INFORMATION

(71) Applicant: INTUITIVE SURGICAL OPERATIONS, INC., Sunnyvale, CA (US)

(72) Inventors: Jonathan Michael Sorger, Belmont, CA (US); Ian E. McDowall, Woodside, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 624 days.

(21) Appl. No.: 17/055,042

(22) PCT Filed: May 14, 2019

(86) PCT No.: PCT/US2019/032191
§ 371 (c)(1),
(2) Date: Nov. 12, 2020

(87) PCT Pub. No.: WO2019/222194
PCT Pub. Date: Nov. 21, 2019

(65) Prior Publication Data
US 2021/0236213 A1 Aug. 5, 2021

Related U.S. Application Data

(60) Provisional application No. 62/671,970, filed on May 15, 2018.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 90/361* (2016.02);
(Continued)

(58) Field of Classification Search
CPC ....... A61B 34/10; A61B 34/25; A61B 90/361; A61B 34/35; A61B 2034/105;
(Continued)

(56) References Cited

U.S. PATENT DOCUMENTS

| 7,769,432 | B2 | 8/2010 | Klimberg et al. |
| 2014/0275974 | A1 | 9/2014 | Samuels |

(Continued)

FOREIGN PATENT DOCUMENTS

| JP | 2015504737 A | 2/2015 |
| WO | WO-2011094659 A2 | 8/2011 |

OTHER PUBLICATIONS

International Search Report and Written Opinion for Application No. PCT/US2019/032191, dated Sep. 23, 2019, 11 pages (ISRG08360/PCT).

(Continued)

*Primary Examiner* — Charlotte M Baker
(74) *Attorney, Agent, or Firm* — HAYNES AND BOONE, LLP

(57) ABSTRACT

A system and method for performing a teleoperational medical procedure is provided. In an example, a medical system includes an imaging instrument, a processor coupled to the imaging instrument, and a non-transitory computer memory coupled to the processor. The non-transitory computer memory stores machine-executable instructions that, when executed, cause the processor to: receive, from the imaging instrument, an image of a patient anatomy, wherein the patient anatomy includes a tissue within a tissue bed; receive an ex vivo model of the tissue after removal of the (Continued)

tissue from the tissue bed; and determine an arrangement of the tissue in the tissue bed from the ex vivo model and the image of the patient anatomy.

20 Claims, 13 Drawing Sheets

(51) Int. Cl.
  *A61B 90/00*    (2016.01)
  *G06T 7/00*     (2017.01)
  *G06T 11/00*    (2006.01)
  *H04N 7/18*     (2006.01)
  *A61B 34/35*    (2016.01)

(52) U.S. Cl.
  CPC ............ *G06T 7/0014* (2013.01); *G06T 11/00* (2013.01); *H04N 7/183* (2013.01); *A61B 34/35* (2016.02); *A61B 2034/105* (2016.02); *A61B 2034/252* (2016.02); *A61B 2090/363* (2016.02); *A61B 2090/365* (2016.02); *G06T 2200/24* (2013.01); *G06T 2207/30004* (2013.01); *G06V 2201/03* (2022.01)

(58) Field of Classification Search
  CPC ........ A61B 2034/252; A61B 2090/363; A61B 2090/365; A61B 34/74; A61B 2090/3614; G06T 7/0014; G06T 11/00; G06T 2200/24; G06T 2207/30004; H04N 7/183; G06V 2201/03
  USPC ........................................................ 382/128
  See application file for complete search history.

(56) References Cited

U.S. PATENT DOCUMENTS

2017/0172668 A1   6/2017  Aljuri et al.
2020/0367818 A1*  11/2020  DaCosta ............ A61K 49/0036

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/032191, dated Nov. 26, 2020, 8 pages.

* cited by examiner

SYSTEMS AND METHODS FOR DETERMINING AN ARRANGEMENT OF EXPLANTED TISSUE AND FOR DISPLAYING TISSUE INFORMATION

CROSS-REFERENCE TO RELATED APPLICATIONS

This application is the U.S. national phase of International Application No. PCT/US2019/032191, filed May 14, 2019, which designated the U.S. and claims priority to and the benefit of U.S. Provisional Application No. 62/671,970, filed May 15, 2018, all of which are incorporated by reference herein in their entirety.

FIELD

The present disclosure is directed to systems and methods for performing a teleoperational medical procedure and more particularly to systems and methods for determining an arrangement of explanted tissue in a tissue bed from which it was excised and displaying pathology information regarding the explanted tissue on an image of the tissue bed in a display of a teleoperational system.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted.

In some exemplary procedures, tissue is removed from the surrounding anatomy, and the explanted tissue is sent for processing by a pathologist. The clinicians involved may balance many factors when determining how much tissue to remove. In general, the intent is to remove all suspicious tissue while minimizing the removal of healthy tissue and minimizing trauma to the surrounding anatomy. However, in the event that the pathologist determines that a surgical margin of the excised tissue is cancerous or otherwise diseased, it may indicate that abnormal cells were left in the patient. Accordingly, additional surgeries may be performed to excise further tissue.

SUMMARY

The embodiments of the invention are summarized by the claims that follow below.

In an embodiment, a medical system includes an imaging instrument, a processor coupled to the imaging instrument, and a non-transitory computer memory coupled to the processor. The non-transitory computer memory stores machine-executable instructions that, when executed, cause the processor to: receive, from the imaging instrument, an image of a patient anatomy, wherein the patient anatomy includes a tissue within a tissue bed; receive an ex vivo model of the tissue after removal of the tissue from the tissue bed; and determine an arrangement of the tissue in the tissue bed from the ex vivo model and the image of the patient anatomy.

In another embodiment, a method includes receiving a model of explanted tissue. The model includes a marked portion of a surgical margin of the explanted tissue. An image of a patient anatomy is received. The patient anatomy includes a tissue bed from which the explanted tissue is removed. A region of the tissue bed that was proximate to the marked portion of the surgical margin prior to removal of the explanted tissue is marked in the image.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
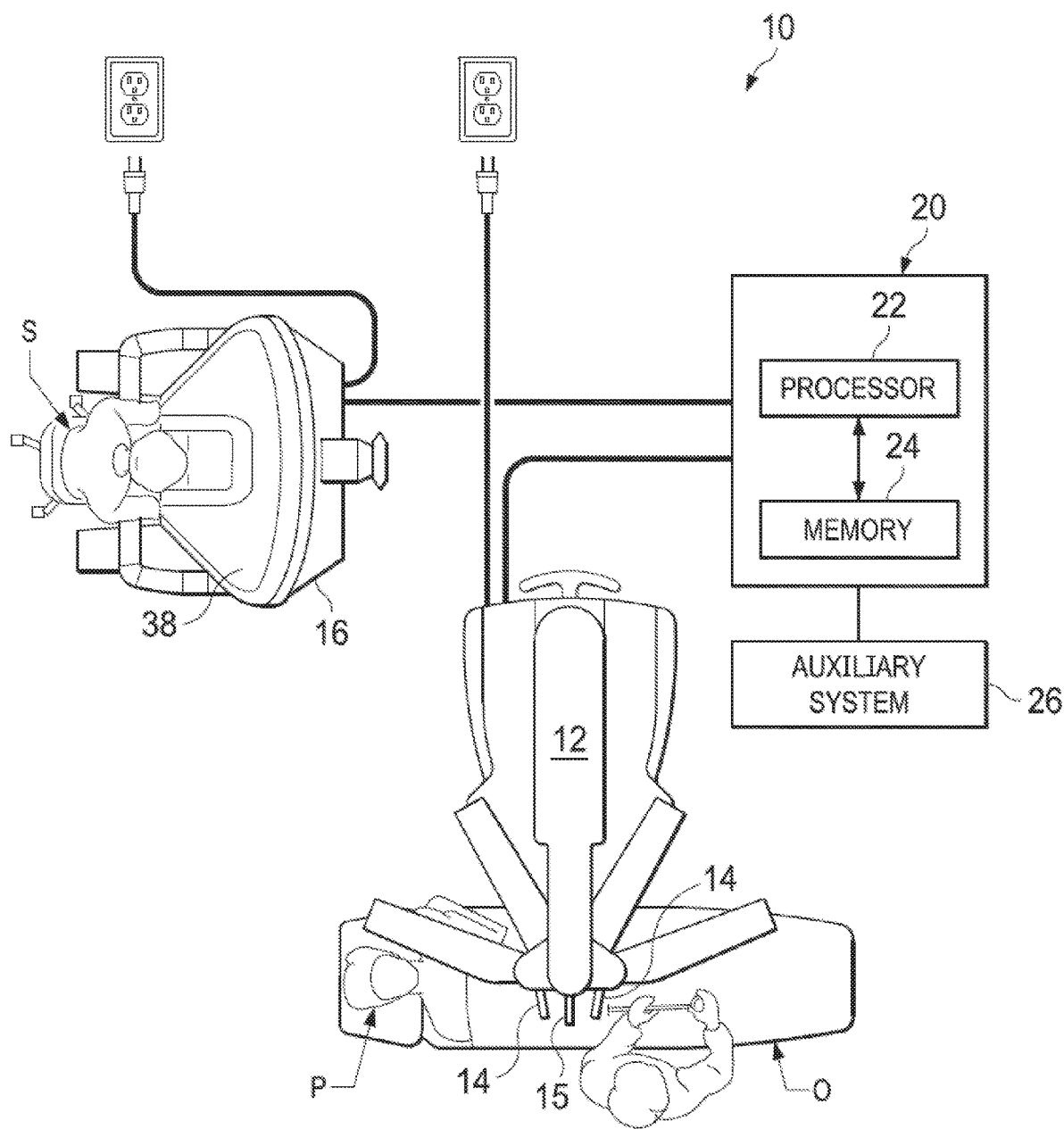
FIG. 1A is a schematic view of a medical system according to some embodiments of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

Although some of the examples described herein often refer to surgical procedures or tools, or medical procedures or tools, the techniques disclosed also apply to non-medical procedures and non-medical tools. For example, the tools, systems, and methods described herein may be used for non-medical purposes including industrial uses, general robotic uses, and sensing or manipulation of non-tissue work pieces. Other example applications involve surgical or non-surgical cosmetic improvements, imaging of or gathering data from human or animal anatomy, training medical or non-medical personnel, performing procedures on tissue removed from human or animal anatomies (without return to a human or animal anatomy), and performing procedures on human or animal cadavers.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a medical system for use in, for example, medical procedures including diagnostic, therapeutic, or surgical procedures, is generally indicated by the reference numeral 10. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As will be described, the medical systems of this disclosure may be teleoperated, non-teleoperated, or hybrid teleoperated under the teleoperational control of a surgeon. In alternative embodiments, a medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the medical system 10 may include a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. In various embodiments, a medical system may include more than one operator input system 16 and surgeon's console. In various embodiments, an operator input system may be available on a mobile communication device including a tablet or a laptop computer. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like.

In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the operator input system 16. An image of the surgical site can be obtained by the endoscopic imaging system 15, such as a stereoscopic endoscope, which can be manipulated by the teleoperational assembly 12 to orient the endoscope 15. A control system 20 can be used to process the images of the surgical site for subsequent display to the surgeon S through the operator input system 16 (can also be referred to as a surgeon's console 16). The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator.

The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulatable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The medical system 10 also includes a control system 20. The control system 20 includes at least one memory 24 and at least one processor 22, and typically a plurality of processors, for effecting control between the medical instrument system 14, the operator input system 16, and other auxiliary systems 26 which may include, for example, imaging systems, audio systems (including an intercom system), fluid delivery systems, display systems, mobile vision carts, illumination systems, steering control systems, irrigation systems, and/or suction systems. The control system 20 also includes programmed instructions (e.g., a computer-readable medium storing the instructions) to implement some or all of the methods described in accordance with aspects disclosed herein.

While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscope 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be co-located, or they may be positioned in separate locations. Multiple operator input systems allow more than one operator to control one or more manipulator assemblies in various combinations.

Figure 1B:
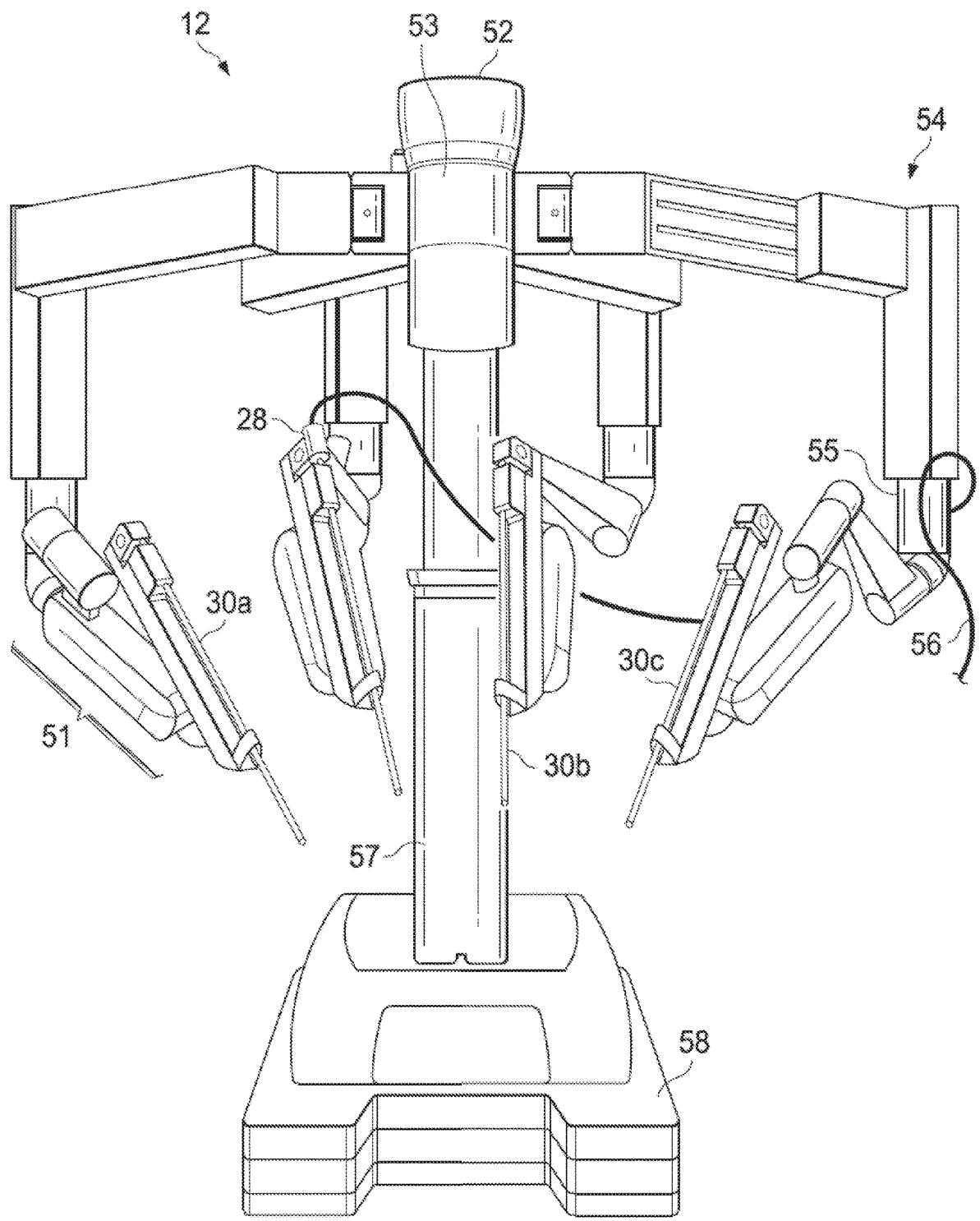
FIG. 1B is a perspective view of a teleoperational manipulator according to some embodiments of the present disclosure.

FIG. 1B is a perspective view of one embodiment of a teleoperational assembly 12 which may be referred to as a patient side cart. The teleoperational assembly 12 shown provides for the manipulation of three surgical tools 30a, 30b, 30c (e.g., instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical site can include images of the distal ends of the surgical tools 30a-c when they are positioned within the field-of-view of the imaging device 28.

The teleoperational assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperational assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 30a with a support structure 59 used to removably attach a cannula that embodies the principles of this disclosure. The manipulator arms 51 may be teleoperatable. In some examples, the arms 54 connecting to the orienting platform are not teleoperatable. Rather, such arms 54 are positioned as desired before the surgeon S begins operation with the teleoperative components.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device acquires image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
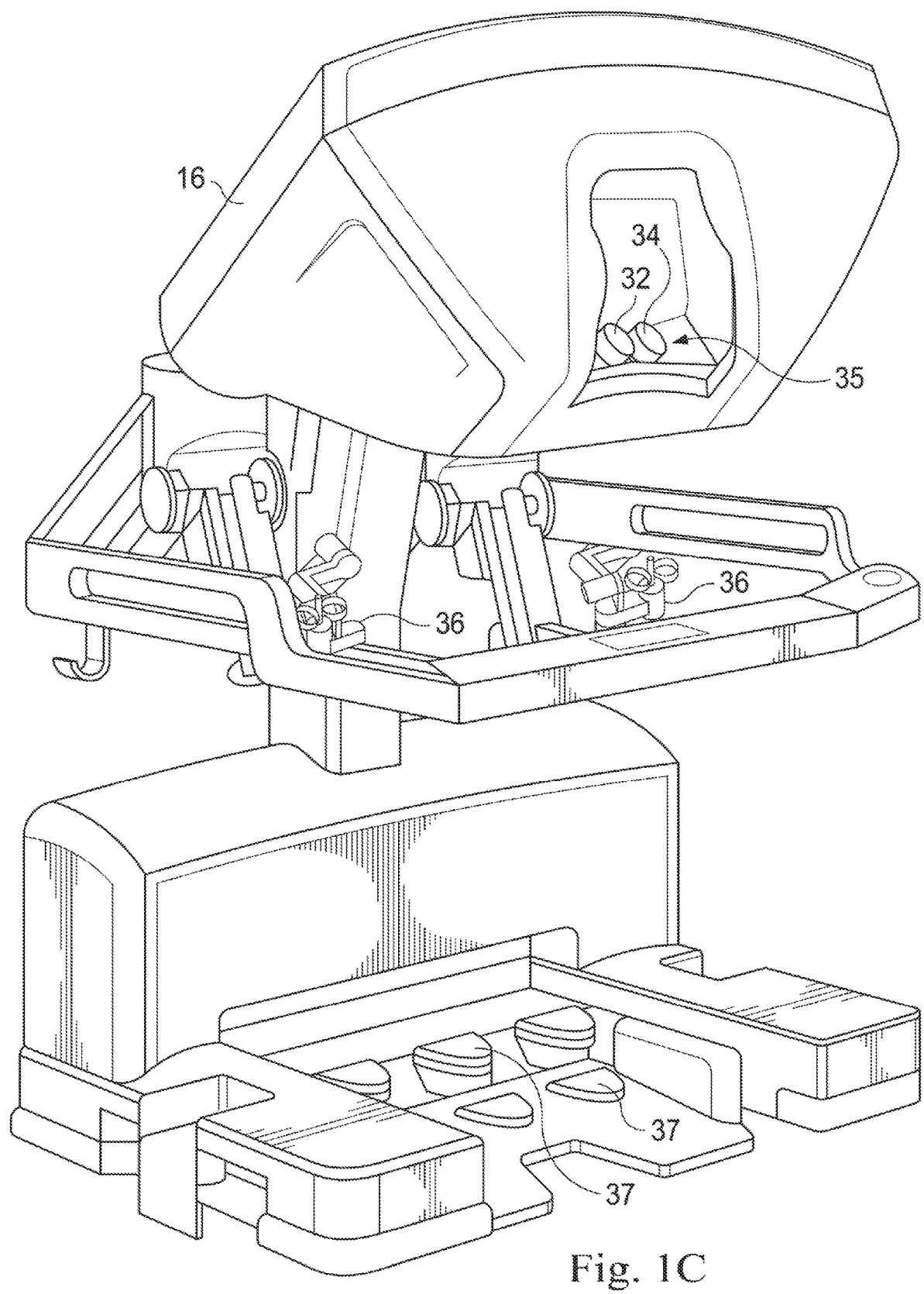
FIG. 1C is a perspective view of a surgeon's control console for a medical system according to some embodiments of the present disclosure.

FIG. 1C is a perspective view of the surgeon's console 16. The surgeon's console 16 includes a left eye display 32 and a right eye display 34 for presenting the surgeon S with a coordinated stereo view of the surgical environment that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot.

As described below, devices, systems, and methods for determining the arrangement of explanted tissue in the tissue bed from which it was excised during teleoperational medical surgeries are provided. The present disclosure provides embodiments in which a medical system 10 captures images of a patient anatomy P prior to and during the removal of tissue. The tissue is analyzed by a pathologist who also captures images of the tissue ex vivo to build a model of the explanted tissue. The pathologist identifies surgical margins of the excised tissue with no or minimal healthy cells between the cancerous or otherwise diseased cells and the margin. Such areas of the margin may be marked in the ex vivo model. The medical system 10 receives the model of the explanted tissue with the marked margins and, utilizing pattern and shape matching, identifies the corresponding regions in the remaining tissue bed. Highlighting, outlines, and other identifiers may be overlaid on live or prerecorded images or video to assist the surgeon S in locating the regions in the tissue bed. The surgeon S may then use the medical system 10 to remove further tissue based on the identifiers. In some examples, this allows the surgeon S to remove a tumor, have it analyzed, and quickly determine whether additional tissue should be removed, often during the course of a single procedure. Although some examples refer to prostatic procedures, the systems and methods of this disclosure are suitable for use in any of a variety of anatomical systems including the colon, the intestines, the lungs, the bladder/kidneys, lymphatic system, or the like.

Figure 2A:
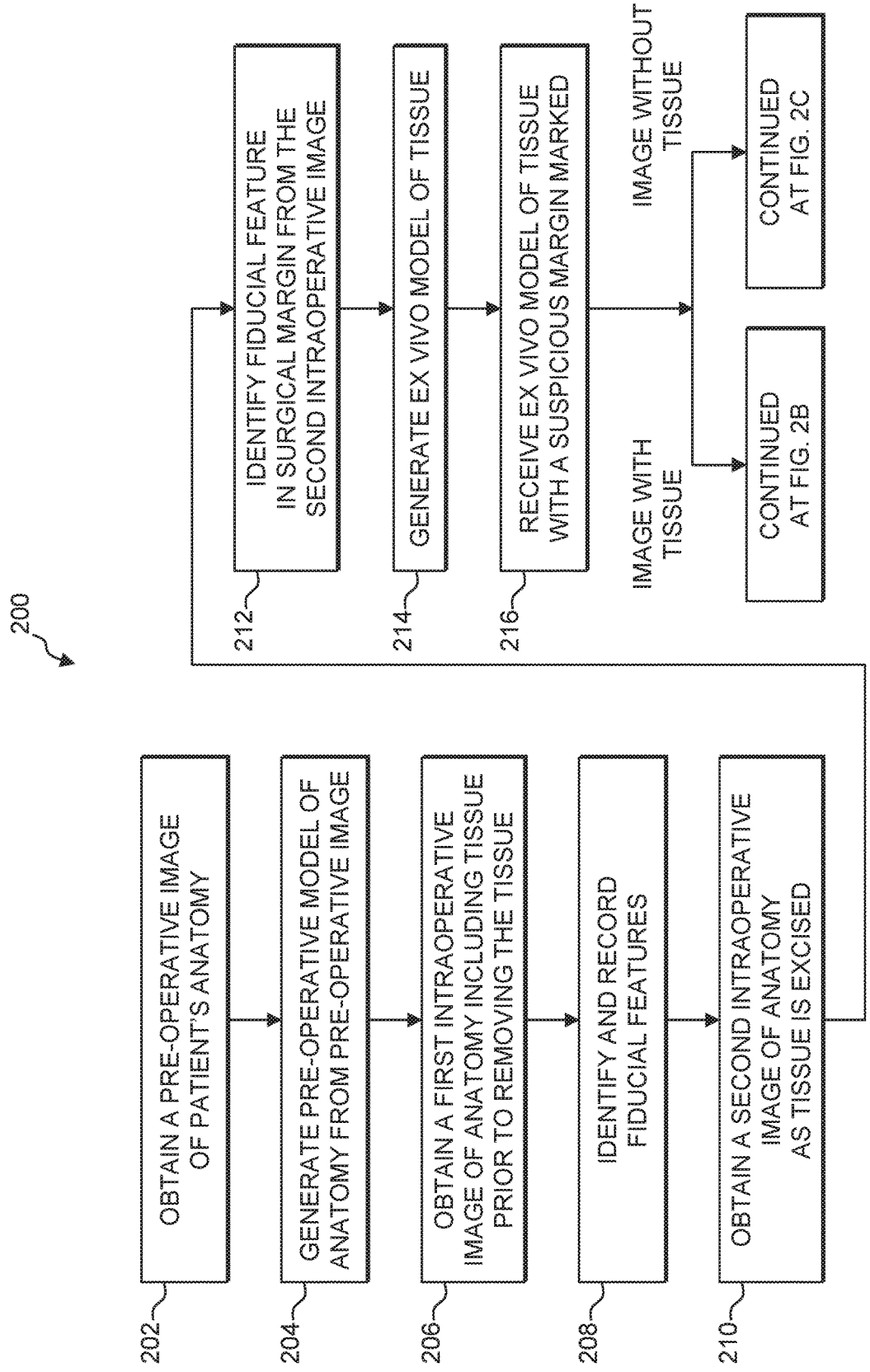
FIGS. 2A-2C are flowcharts describing a method for correlating excised tissue with the anatomy from which it was excised according to some embodiments of the present disclosure.
Figures 2B, 2C:
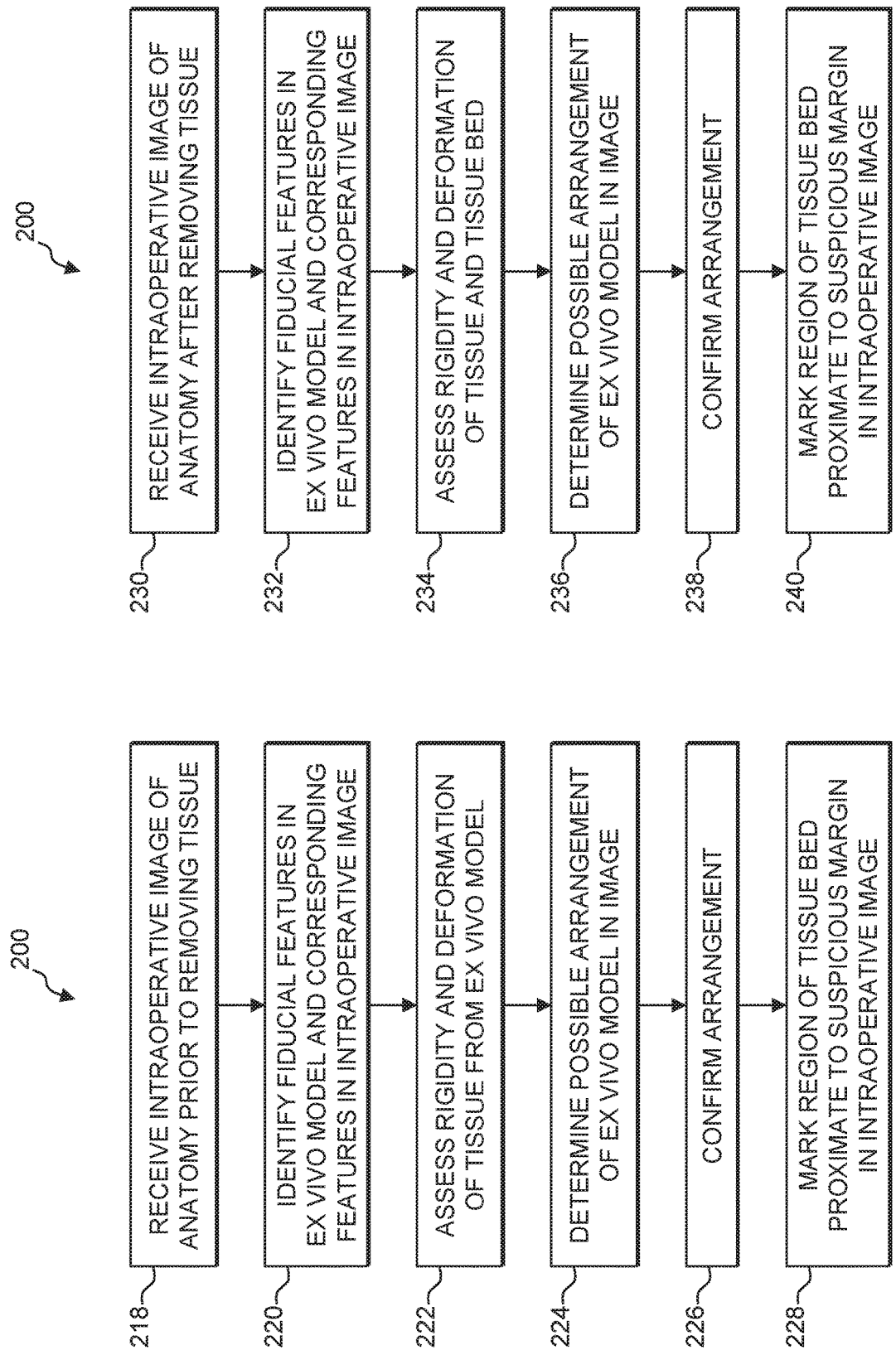
Figure 3:
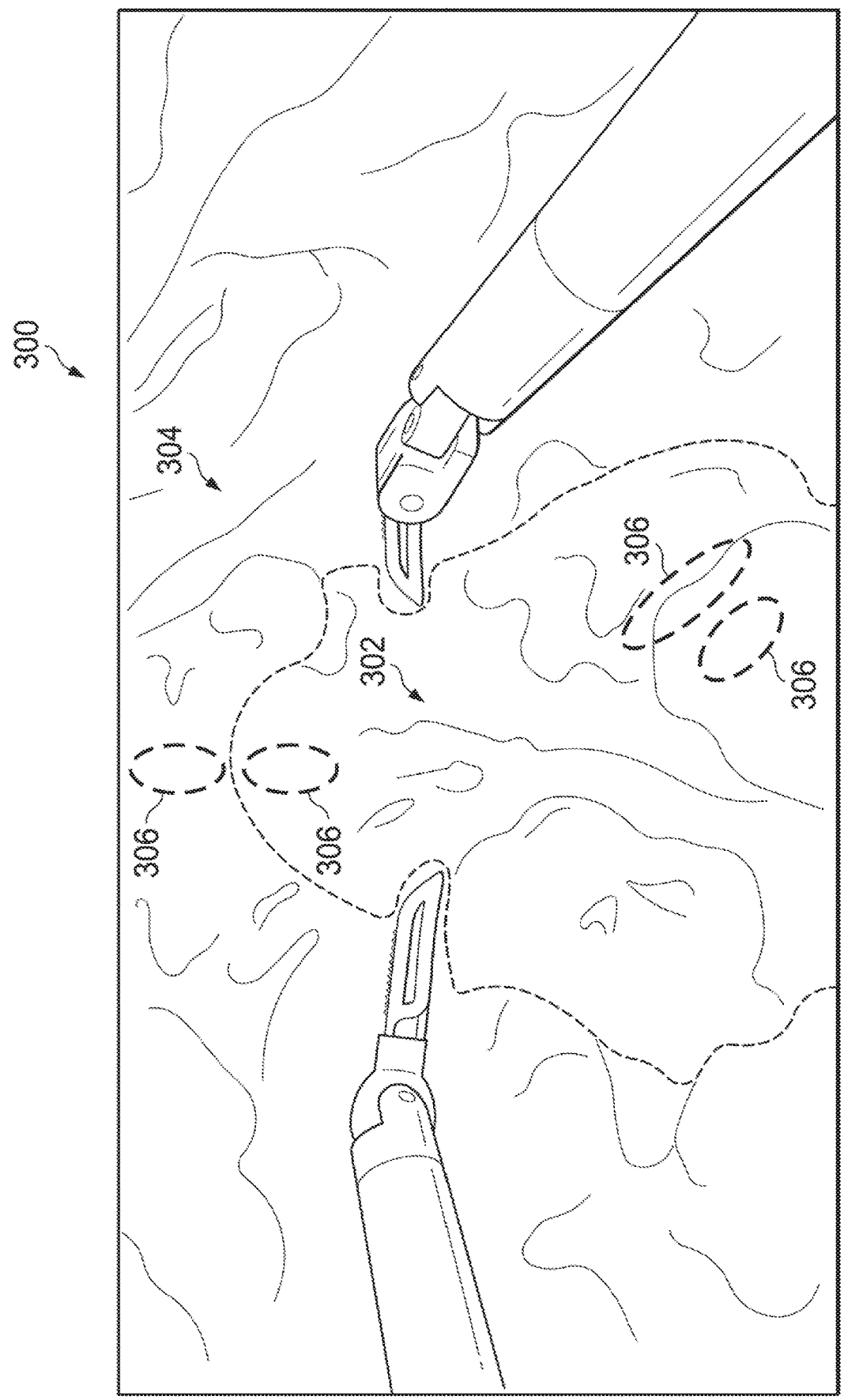
FIG. 3 illustrates an intraoperative image of patient anatomy including a tissue to be excised according to some embodiments of the present disclosure.
Figure 4:
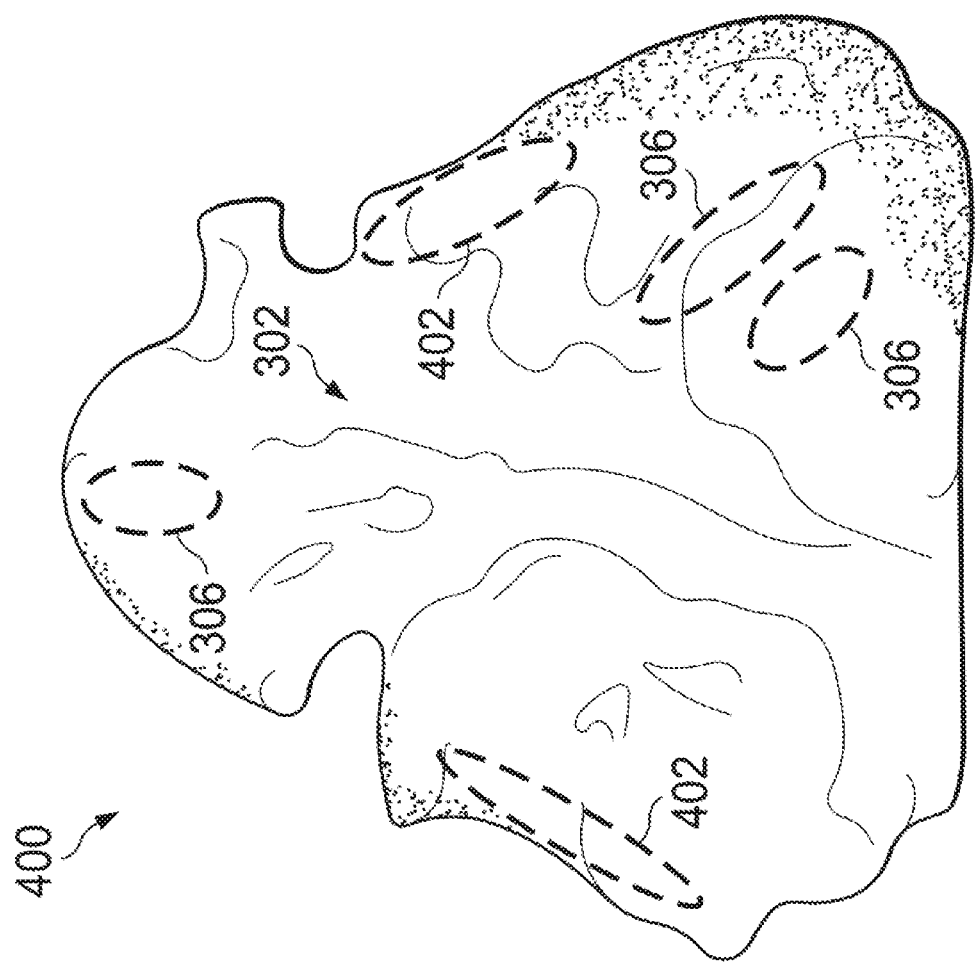
FIG. 4 illustrates an ex vivo model of excised tissue according to some embodiments of the present disclosure.
Figure 5:
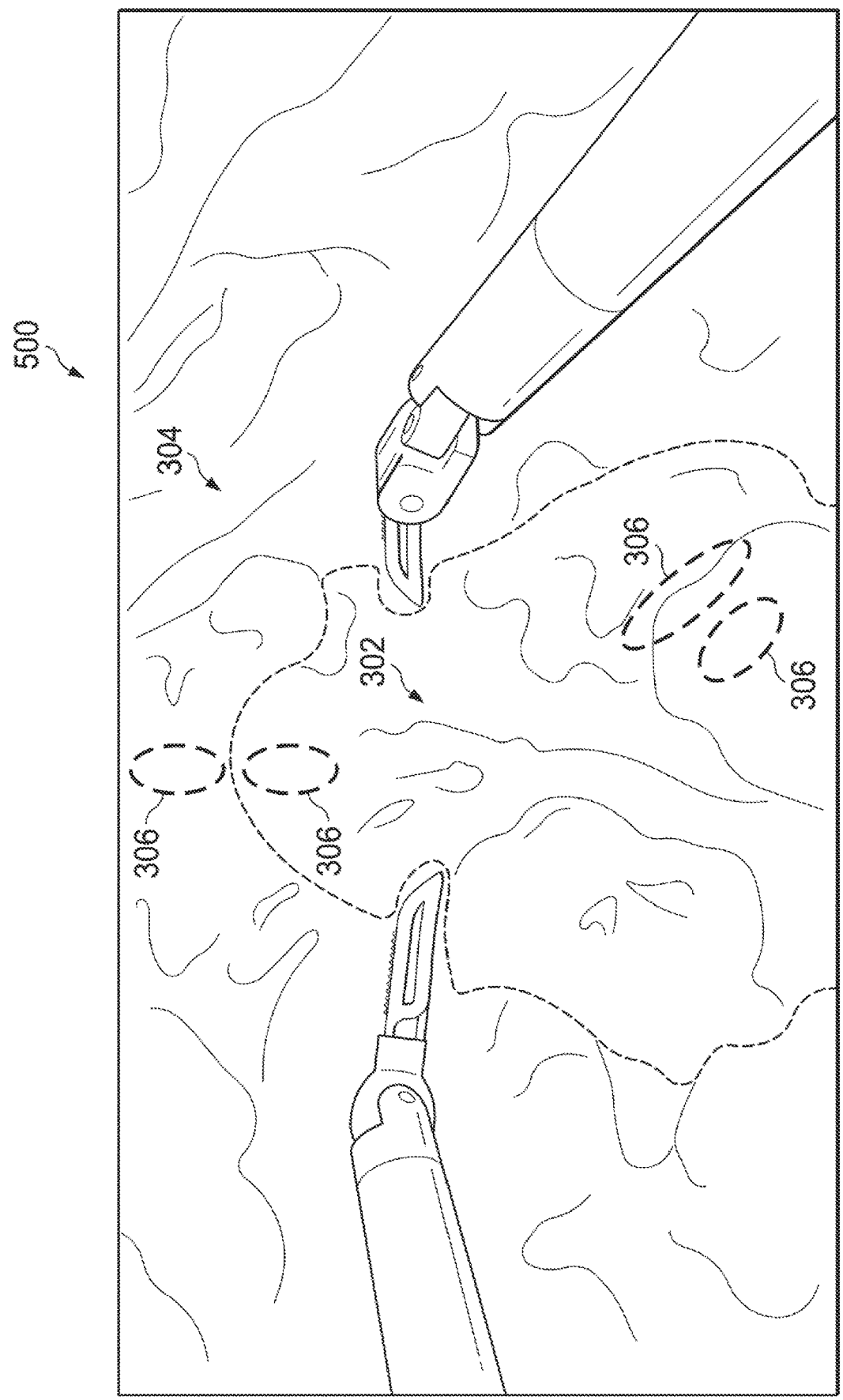
FIG. 5 illustrates an intraoperative image of patient anatomy according to some embodiments of the present disclosure.
Figure 6:
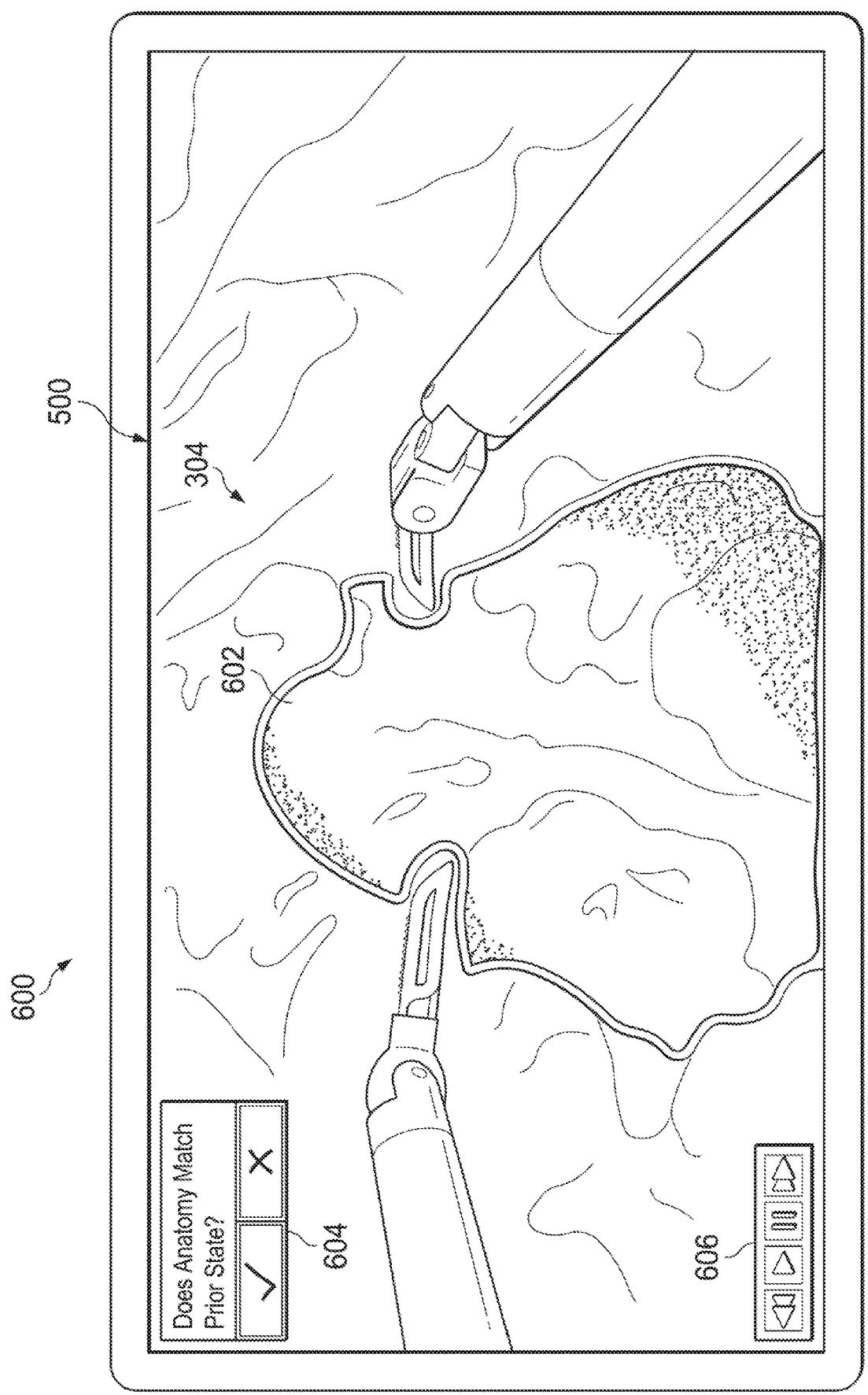
FIG. 6 illustrates a graphical user interface providing a request for confirmation of an arrangement of tissue according to some embodiments of the present disclosure.
Figure 7:
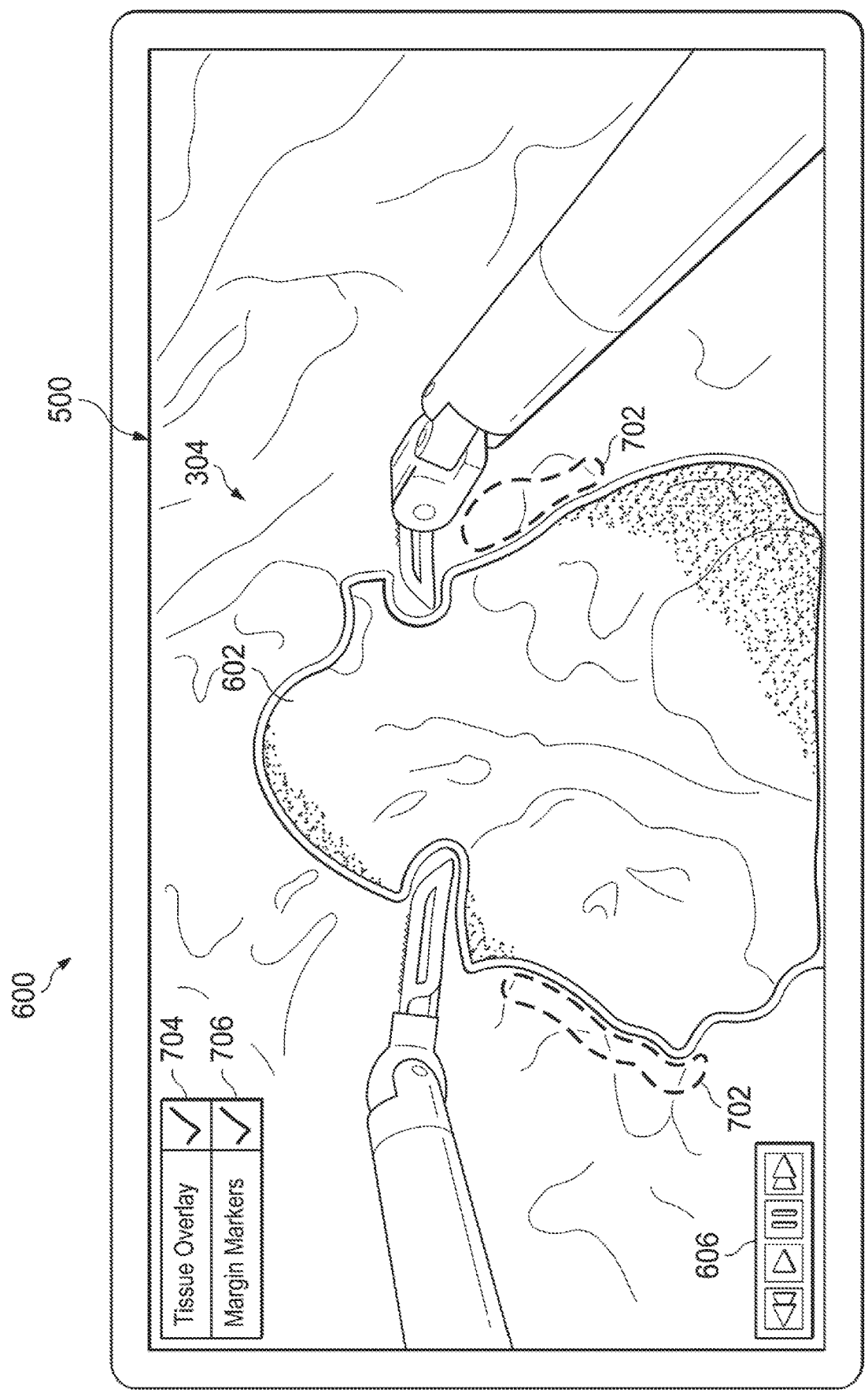
FIG. 7 illustrates a graphical user interface displaying tissue according to some embodiments of the present disclosure.
Figure 8:
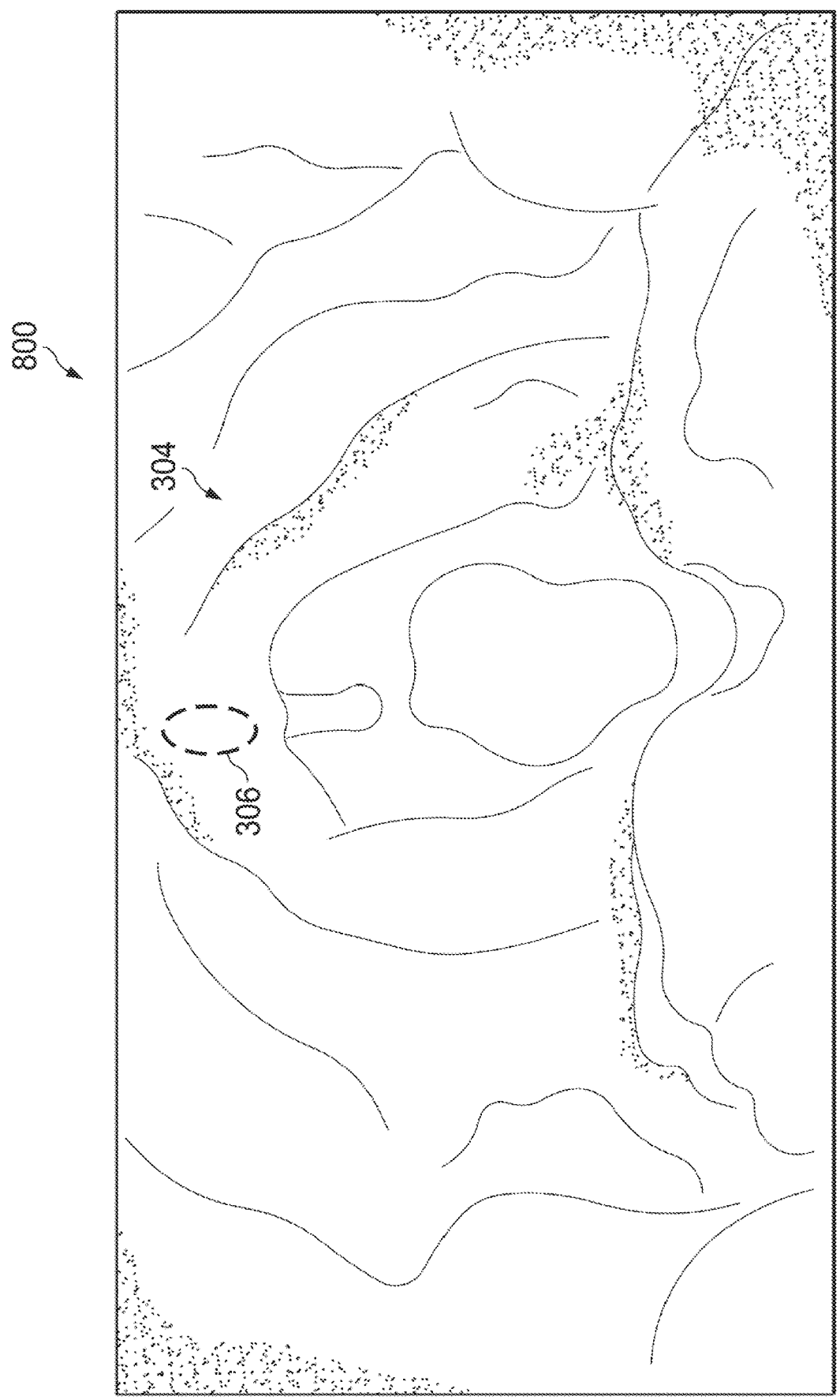
FIG. 8 illustrates an intraoperative image of patient anatomy with tissue having been excised according to some embodiments of the present disclosure.
Figure 9:
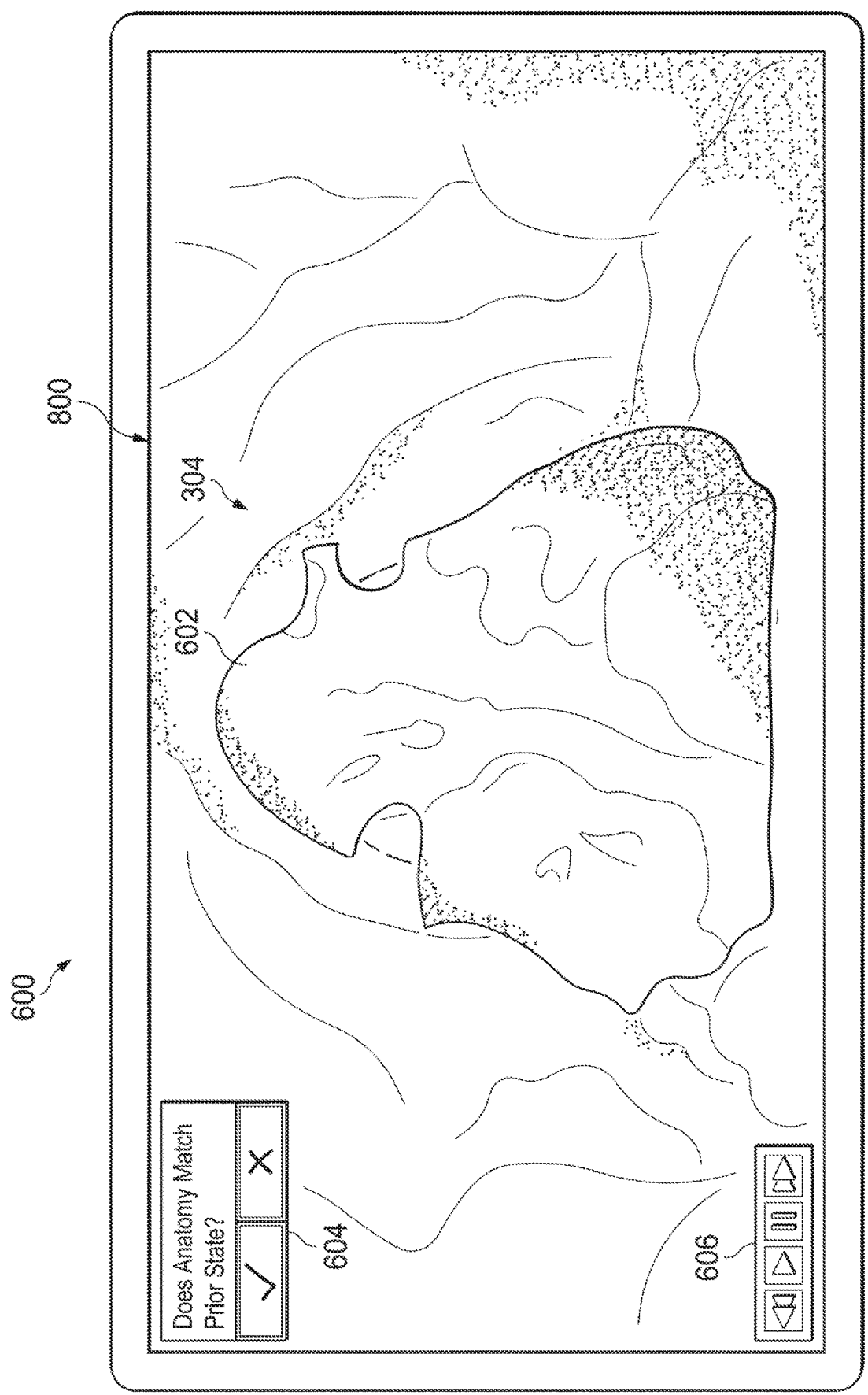
FIG. 9 illustrates a graphical user interface providing a request for confirmation of an arrangement of tissue according to some embodiments of the present disclosure.
Figure 10:
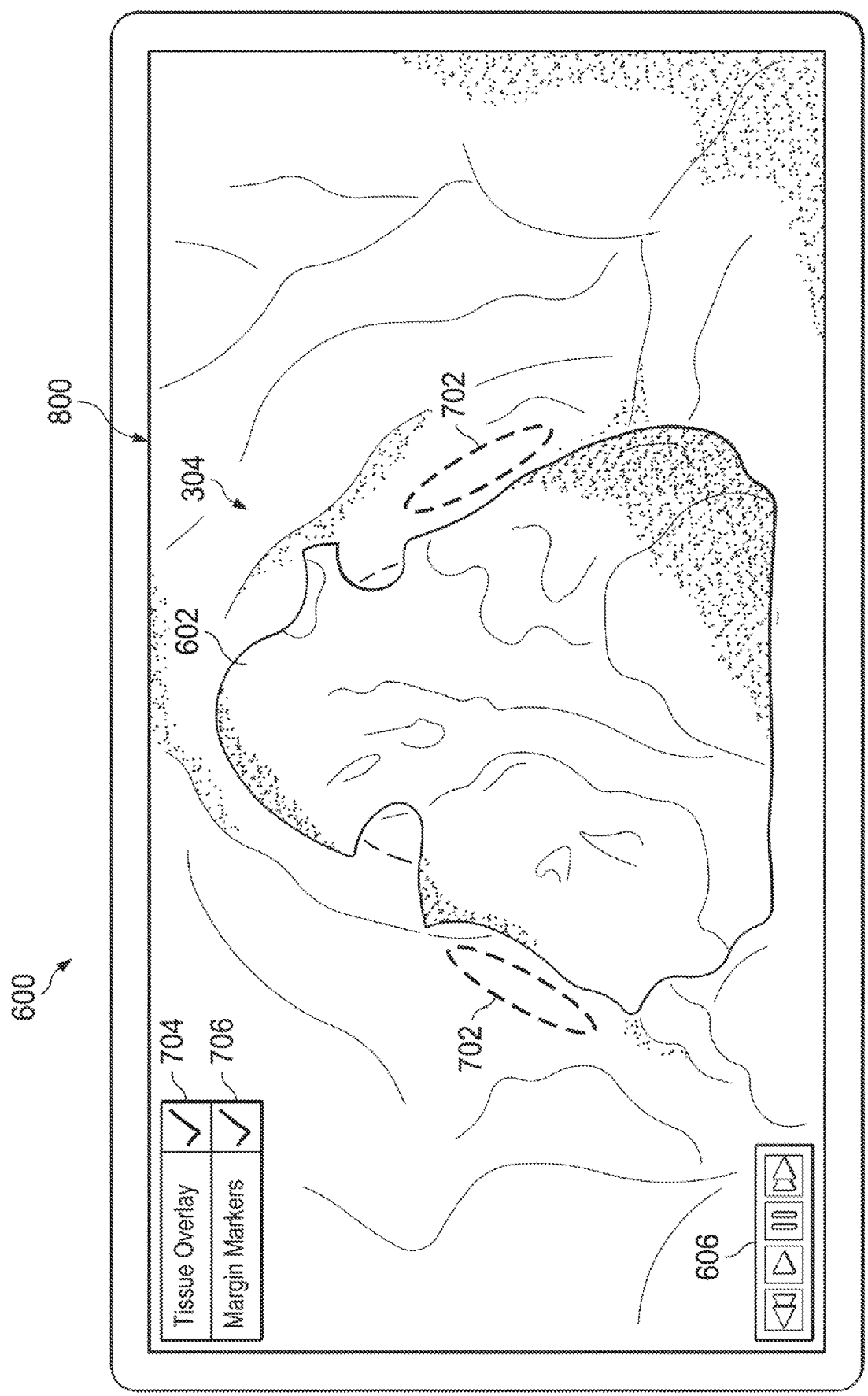
FIG. 10 illustrates a graphical user interface displaying tissue according to some embodiments of the present disclosure.

Examples of the devices, systems, and methods are described with reference to FIGS. 2A-10. In that regard, FIGS. 2A-2C are flowcharts describing a method 200 for correlating excised tissue with the anatomy from which it was excised according to some embodiments of the present disclosure. The method 200 is illustrated in FIGS. 2A-2C as a set of operations or processes. Not all of the illustrated processes may be performed in all embodiments of method 200. Additionally, one or more processes that are not expressly illustrated in FIGS. 2A-2C may be included before, after, in between, or as part of the illustrated processes. In some embodiments, one or more of the processes of method 200 may be implemented, at least in part, in the form of executable code stored on non-transitory, tangible, machine-readable media that, when run by one or more processors (e.g., the processors of control system 20) may cause the one or more processors to perform one or more of the processes. FIG. 3 illustrates an intraoperative image of patient anatomy P including a tissue to be excised according to some embodiments of the present disclosure. FIG. 4 illustrates an ex vivo model of the excised tissue according to some embodiments of the present disclosure. FIG. 5 illustrates an intraoperative image of the patient anatomy P according to some embodiments of the present disclosure. FIG. 6 illustrates a graphical user interface providing a request for confirmation of an arrangement of the tissue according to some embodiments of the present disclosure. FIG. 7 illustrates the graphical user interface displaying the tissue according to some embodiments of the present disclosure. FIG. 8 illustrates an intraoperative image of the patient anatomy P with the tissue excised according to some embodiments of the present disclosure. FIG. 9 illustrates the graphical user interface providing a request for confirmation of an arrangement of the tissue according to some embodiments of the present disclosure. FIG. 10 illustrates the graphical user interface displaying the tissue according to some embodiments of the present disclosure.

Referring first to FIG. 2A, at process 202, a pre-operative image of a region of a patient's anatomy may be obtained. The image may be used to generate a pre-operative model of the patient anatomy P, and this process is optional in some examples of the present disclosure. In examples that include process 202, the image may capture any suitable anatomic region for planning a medical procedure and may include areas involved in the medical procedure as well as any surrounding areas. In some examples, the imaged region includes a portion of tissue (e.g., a tumor) to be excised in a teleoperational surgical procedure.

The pre-operative image may be obtained by magnetic resonance imaging (MRI), computed tomography (CT), fluoroscopy, thermography, ultrasound, optical coherence tomography (OCT), thermal imaging, impedance imaging, laser imaging, nanotube X-ray imaging, and/or other suitable imaging procedures. In some embodiments, the pre-operative imaging obtains two-dimensional images from multiple perspectives that are combined into a three-dimensional image. Thus, the pre-operative image may correspond to a two-dimensional, a three-dimensional, or a four-dimensional (e.g., time-based or velocity-based information)

image of the anatomy. Furthermore, the pre-operative image may include a still image and/or a frame of video.

At process 204, a pre-operative model of the patient anatomy P may be generated from the imaging data obtained in process 202. The model may contain part of or an entire anatomic organ or anatomic region, and in an example, the pre-operative model includes the tissue to be excised and a tissue bed from which it is to be removed. As noted above, pre-operative imaging and generating a pre-operative model may be optional in some examples.

Referring to process 206 of FIG. 2A and to FIG. 3 a first intraoperative image 300 is obtained during the teleoperational procedure prior to the target tissue 302 being excised from a tissue bed 304. In various examples, the first intraoperative image 300 is a still image or a frame of video and depicts the patient anatomy P as a flat (2D) representation, a stereoscopic representation, a 3D representation, a 4D (e.g., time-based or velocity-based) representation, or other suitable depiction. The first intraoperative image 300 may be obtained by an imaging instrument (e.g., endoscopic imaging system 15) coupled to the teleoperational assembly 12, other imaging instruments within the patient anatomy P, cameras positioned outside of the patient P, and/or any other suitable source.

The first intraoperative image 300 may be displayed in real time on the surgeon's console 16 and at any other suitable display during the procedure. Additionally, the first intraoperative image 300 may be captured and stored by the control system 20 to be played back at a later time. As described in more detail below, the first intraoperative image 300 may be augmented to assist the surgeon S during the teleoperational procedure. In a particular embodiment, once the target tissue 302 has been removed and analyzed, the first intraoperative image 300 is augmented to indicate a region in the patient anatomy P that corresponds to a suspicious surgical boundary of the target tissue 302 so that further tissue may be removed.

Referring to process 208 of FIG. 2A and referring still to FIG. 3, prior to the removal of the target tissue 302, fiducial features 306 of the target tissue 302 and/or the surrounding patient anatomy P in the first intraoperative image 300 are identified and recorded in order to determine the arrangement (e.g., orientation, alignment, shape, etc.) of the target tissue 302 in the tissue bed 304 after the tissue 302 has been removed. The fiducial features 306 may include naturally occurring features as well as those created by the surgeon S. For example, naturally occurring fiducial features 306 include easily identifiable variations in color, texture, vascularity, structure, etc. Additionally or in the alternative, the surgeon S may create fiducial features 306 using a dye, a cautery, a shallow incision, or other suitable technique to leave a temporary or indelible mark on the tissue.

The medical system 10 may automatically identify the fiducial features from the first intraoperative image 300. Additionally or in the alternative, the surgeon S may utilize the control system 20 of the medical system 10 to identify, mark, and record some of the fiducial features. Once identified, the pre-operative model of processes 202 and 204 may be updated to include the identified fiducial features 306.

The surgeon S may remove the target tissue 302 from the tissue bed 304 using the instrument system 14 of the medical system 10. The surgeon S may use a combination of scalpels, blades, cauteries, laser tools, cryogenic tools, and/or other tools to excise the target tissue 302.

Referring to process 210, a second intraoperative image of the anatomy may be obtained as the target tissue 302 is separated from the tissue bed 304. The second intraoperative image may be used to identify further fiducial features, which is optional in some examples. In various examples where the second intraoperative image is obtained, the second image is a still image or a frame of video and depicts the patient anatomy P as a flat (2D) representation, a stereoscopic representation, a 3D representation, a 4D (e.g., time-based or velocity-based) representation, or other suitable depiction. The second intraoperative image may be obtained by an imaging instrument (e.g., endoscopic imaging system 15) coupled to the teleoperational assembly 12, other imaging instruments within the patient anatomy P, cameras positioned outside of the patient P, and/or any other suitable source. In capturing the second intraoperative image, information may be obtained from the imaging instrument such as camera pose, camera position, and/or camera movement information. The second intraoperative image depicts the surgical margin of the target tissue 302 as the target tissue 302 is separated from the tissue bed 304. Accordingly in process 212, the medical system 10 may perform shape recognition on the margin in the second intraoperative image to identify distinguishing shapes made by the surgeon's tools that may act as fiducial features 306. For example, the path of a cautery may leave a distinct shape in the tissue 302 and/or the tissue bed 304 that may be used to determine the arrangement of the tissue 302 in the tissue bed 304. As noted above, processes 210 and 212 are optional. For example, the first intraoperative image may provide sufficient fiducial features.

The removed tissue 302 may be prepared and analyzed by a pathologist such as a general pathologist, a histologist, or a cytologist. The pathologist determines histologic or cytologic information about the removed tissue 302. In an example, the pathologist identifies suspected cancerous cells or other abnormal conditions.

Referring to process 214 of FIG. 2A and to FIG. 4, an ex vivo model 400 of the removed tissue 302 is generated. In some embodiments, this includes taking one or more photographic images of the explanted tissue 302, although any other suitable imaging modality may be used. The ex vivo model 400 may include a 2D or 3D representation of the removed tissue 302 and may include the exterior surface (including the surgical margin), internal or external fiducial features 306, and/or any suitable identifying structures such as blood vessels or other passageways. As the explanted tissue 302 has been manipulated during the course of the procedure, the shape of the tissue 302 in the ex vivo model 400 may differ significantly from the shape of the tissue 302 in the pre-operative model and the shape in any images taken before the tissue has been excised (e.g., the first intraoperative image 300 and/or the second intraoperative image).

The pathologist may note on the ex vivo model 400 those regions on the exterior of the target tissue 302 where disease is present or where disease is separated from the exterior by an amount of healthy tissue that is less than a minimum threshold (e.g., 1 mm, 2 mm, etc.). Some such areas 402 are represented by markers such as dotted lines or other indicators of suspicious margins or diseased tissue. The surgeon S may use this information during the teleoperational procedure to identify and remove further tissue.

Referring to process 216, the medical system 10 receives the pre-operative model and the ex vivo model 400 with the marked regions 402 and performs shape recognition on a live or prerecorded image of the surgical site to align the ex vivo model 400 to the location of the tissue in the image.

In some examples, the medical system 10 performs shape recognition on a prerecorded image of the surgical site obtained when the tissue 302 is still within the tissue bed 304. By annotating the image to show the location of the suspicious margin, the system 10 may allow the surgeon to review the procedure to see where the margin was located pre-operatively and how the margin was formed. Processes 218-228 of FIG. 2B represent exemplary techniques that may be used for shape recognition on a prerecorded image of the surgical site with the target tissue 302 still in place.

In some examples, the medical system 10 performs shape recognition on a prerecorded or live image of the surgical site with the tissue bed 304 obtained after the tissue 302 is removed. By annotating the image to show the location of the suspicious margin, the system 10 may allow the surgeon to visualize the current location of the corresponding margin in the tissue bed 304 and to take further corrective actions. Processes 230-240 of FIG. 2C represent exemplary techniques that may be used for shape recognition on a prerecorded or live image where the target tissue 302 has been removed.

Referring first to process 218 of FIG. 2B and to FIG. 5, the medical system 10 receives an intraoperative image 500 of patient anatomy P obtained prior to the tissue 302 being removed, such as the first intraoperative image 300 of process 206. The image 500 may be a frame of video and may depict the patient anatomy P as a flat (2D) representation, a stereoscopic representation, a 3D representation, a 4D (e.g., time-based or velocity-based) representation, or other suitable depiction. The image 500 may be obtained by any suitable imaging device such as an imaging instrument of the medical system 10.

Referring to process 220, the medical system 10 identifies natural and/or artificial fiducial features 306 in the ex vivo model 400 and their corresponding fiducial features 306 in the intraoperative image 500. These may include the fiducial features 306 formed along the margin of the tissue 302 or tissue bed 304 by the removal of the tissue 302.

Referring to process 222, the medical system 10 may optionally determine the rigidity of the tissue 302 from the ex vivo model 400 and assesses the deformation of the tissue 302. As noted above, the shape of the explanted tissue 302 may be significantly deformed by the procedure. Accordingly, the medical system 10 may perform a deformation analysis to determine one or more potential shapes of the tissue 302 when it was attached to the tissue bed 304.

Referring to process 224, the medical system 10 identifies a possible arrangement (alignment, orientation, deformation, etc.) of the ex vivo model 400 in the image based on the deformation information and/or the fiducial features 306 of the ex vivo model 400, those of the tissue 302 in the image, and/or those of the tissue bed 304 in the image. Additionally or in the alternative, position and location information obtained from the imaging instrument when the tissue 302 was excised is used to determine the possible arrangement.

Referring to process 226, the medical system 10 provides a request for confirmation of the possible arrangement of the ex vivo model 400. The request may be provided at a graphical user interface by the control system 20 on the surgeon's console 16 or by other suitable system and display. Examples of a graphical user interface 600 for this purpose are shown in FIG. 6.

The graphical user interface 600 displays the intraoperative image 500, and may display a representation of the ex vivo model 400 overlaid on the intraoperative image 500. In various such examples, the ex vivo model is represented by a rendering, a wireframe, a cross section, and/or other suitable representation 602 overlaid on the intraoperative image 500. The graphical user interface 600 provides a control 604 (e.g., buttons, prompts, check boxes, etc.) for approving or rejecting the arrangement represented by the overlay 602. In this way, the surgeon S can assess whether the arrangement of the ex vivo model 400 matches that of the tissue 302 in the image. In some embodiments, the intraoperative image 500 is a frame of a video, and the graphical user interface 600 provides playback controls 606 for the video such as play, rewind, and advance. The medical system 10 providing the graphical user interface 600 may also save the intraoperative image 500 with or without the overlay 602 of the ex vivo model 400 for review at a later time.

If the surgeon S determines that the alignment and orientation is incorrect, the method 200 may return to process 220 and determine a next-nearest arrangement. Conversely, referring to process 228 of FIG. 2B and referring to FIG. 7, when the surgeon S approves the arrangement, the graphical user interface 600 of the medical system 10 may mark the region 702 in the tissue bed 304 that corresponds to a suspicious margin 402 marked in the ex vivo model 400. In an example procedure, region 702 represents an area of the tissue bed 304 adjacent the margin 402 where cancerous cells of the excised tissue 302 met the remaining tissue bed 304. The graphical user interface 600 may indicate the region 702 in the tissue bed 304 by color, outline, a flag and connector, emphasis, de-emphasis, and/or other suitable indicator of the region 702 in the image 600 to aid in identification. In an example, the graphical user interface 600 provides controls 704 and 706 for hiding or displaying the overlay 602 of the ex vivo model 400 and the region indicators 702, respectively. The image 500 with the marked region 702 and the overlay 602 of the ex vivo model 400 may be displayed on the surgeon's console 16 and at any other suitable display and may be saved for review at a later time.

Based on the image 500, the surgeon S may perform additional teleoperational surgical procedures using the medical system 10 such as further excising the marked region 702 of the tissue bed 304. In some examples, by rapidly providing pathology information in the form of an annotated surgical image, the medical system 10 allows the surgeon S to take such further surgical actions in the course of a single operative procedure.

As noted above, the medical system 10 may also provide this pathology information in the context of a live or prerecorded intraoperative image taken after the tissue 302 has been excised. This type of image may provide improved visualization of the tissue bed 304. Referring to process 230 of FIG. 2C and to FIG. 8, the medical system 10 receives an intraoperative image 800 of the patient anatomy P obtained after the tissue 302 is removed. The intraoperative image 800 may be a frame of video and may depict the patient anatomy P as a flat (2D) representation, a stereoscopic representation, a 3D representation, a 4D (e.g., time-based or velocity-based) representation, or other suitable depiction. The image 800 may be obtained by an imaging instrument of the medical system 10.

Referring to process 232, the medical system 10 identifies natural and/or artificial fiducial features 306 in the ex vivo model 400 and any corresponding fiducial features 306 in the tissue bed 304 of intraoperative image 800. These may include the fiducial features 306 formed along the margin of the tissue 302 or tissue bed 304 by the removal of the tissue 302. This may be performed substantially as described in process 220.

Referring to process 234, the medical system 10 may optionally determine the rigidity of the tissue 302 from the ex vivo model 400 and assesses the deformation of the tissue 302. This may be performed substantially as described in process 222. The medical system 10 may also determine the rigidity of the tissue bed 304 to assess deformation of the tissue bed 304 once the tissue has been removed. This may include determining deformation of the tissue bed due to other intervening surgical actions.

Referring to process 236, the medical system 10 identifies a possible arrangement (alignment, orientation, deformation, etc.) of the ex vivo model 400 in the image 800 based on the deformation information and/or the fiducial features 306 of the ex vivo model 400 and/or those of the tissue bed 304 in the image. Additionally or in the alternative, position and location information obtained from the imaging instrument when the tissue 302 was excised is used to determine the possible arrangement. This may be performed substantially as described in process 224.

Referring to process 238, the medical system 10 provides a request for confirmation of the possible arrangement of the ex vivo model 400. The request may be provided at a graphical user interface by the control system 20 on the surgeon's console 16 or by other suitable system and display. This may be performed substantially as described in process 226. Examples of a graphical user interface 600 for this purpose are shown in FIG. 9.

The graphical user interface 600 displays the intraoperative image 800, and may display a representation of the ex vivo model 400 overlaid on the intraoperative image 800. In various such examples, the ex vivo model is represented by a rendering, a wireframe, a cross section, and/or other suitable representation 602 overlaid on the intraoperative image 800. The graphical user interface 600 provides a control 604 (e.g., buttons, prompts, check boxes, etc.) for approving or rejecting the arrangement represented by the overlay 602. In this way, the surgeon S can assess whether the arrangement of the ex vivo model 400 matches that of the tissue 302 in the image. In some embodiments, the intraoperative image 800 is a frame of a video, and the graphical user interface 600 provides playback controls 606 for the video such as play, rewind, and advance. The medical system 10 providing the graphical user interface 600 may also save the intraoperative image 800 with or without the overlay 602 of the ex vivo model 400 for review at a later time.

If the surgeon S determines that the alignment and orientation is incorrect, the method 200 may return to process 234 and determine a next-nearest arrangement. Conversely, referring to process 240 of FIG. 2C and referring to FIG. 10, when the surgeon S approves the arrangement, the graphical user interface 600 of the medical system 10 may mark the region 702 in the tissue bed 304 that corresponds to a suspicious margin 402 marked in the ex vivo model 400. In an example procedure, region 702 represents an area of the tissue bed 304 where cancerous cells of the excised tissue 302 met the remaining tissue bed 304. The graphical user interface 600 may indicate the region 702 in the tissue bed 304 by color, outline, a flag and connector, emphasis, de-emphasis, and/or other suitable indicator of the region 702 in the image 800 to aid in identification. In an example, the graphical user interface 600 provides controls 704 and 706 for hiding or displaying the overlay 602 of the ex vivo model 400 and the region indicators 702, respectively. The image 800 with the marked region 702 and the overlay 602 of the ex vivo model 400 may be displayed on the surgeon's console 16 and at any other suitable display and may be saved for review at a later time.

Based on the image 800, the surgeon S may perform additional teleoperational surgical procedures using the medical system 10 such as further excising the marked region 800 of the tissue bed 304.

One or more elements in embodiments of the invention may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
an imaging instrument;
a processor coupled to the imaging instrument; and
a non-transitory computer memory coupled to the processor that stores machine-executable instructions that, when executed, cause the processor to:
receive, from the imaging instrument, an image of a patient anatomy, wherein the patient anatomy includes a tissue within a tissue bed;
receive an ex vivo model of the tissue; and
determine an arrangement of the tissue in the tissue bed from the ex vivo model and the image of the patient anatomy.

2. The medical system of claim 1, wherein the ex vivo model includes a marked portion of a margin of the tissue, and wherein the non-transitory computer memory stores further machine-executable instructions that cause the processor to:
determine, from the arrangement of the tissue, a region of the tissue bed adjacent to the marked portion of the margin of the tissue prior to removal of the tissue; and
annotate the image with an indicator of the region.

3. The medical system of claim 2, wherein the indicator is from a group consisting of: a color, an outline, a flag, emphasis, and de-emphasis.

4. The medical system of claim 1, wherein the instructions to determine the arrangement of the tissue in the tissue bed include instructions to assess deformation of the tissue bed once the tissue is removed from the tissue bed.

5. The medical system of claim 1, wherein the instructions to determine the arrangement of the tissue in the tissue bed include instructions to:
  determine a possible arrangement of the tissue in the tissue bed;
  display the image with an indicator of the ex vivo model arranged in the possible arrangement; and
  provide a control to confirm the possible arrangement.

6. The medical system of claim 1, wherein the non-transitory computer memory stores further machine-executable instructions that cause the processor to:
  annotate the image with an overlay of the ex vivo model; and
  provide a control to select between hiding and showing the overlay.

7. The medical system of claim 1, wherein the image is of the patient anatomy prior to removal of the tissue from the tissue bed.

8. The medical system of claim 1, wherein the image is of the patient anatomy after removal of the tissue from the tissue bed.

9. The medical system of claim 1, wherein the instructions to determine the arrangement of the tissue in the tissue bed are to determine based on a feature from a group consisting of: a fiducial feature of the tissue, a fiducial feature of the tissue bed, and a fiducial feature caused by removal of the tissue from the tissue bed.

10. The medical system of claim 9, wherein the non-transitory computer memory stores further machine-executable instructions that cause the processor to:
  obtain another image of the tissue in the tissue bed; and
  identify the fiducial feature caused by removal of the tissue from the tissue bed from the another image of the tissue in the tissue bed.

11. The medical system of claim 1, wherein the instructions to determine the arrangement of the tissue in the tissue bed include instructions to assess deformation of the tissue once it is removed from the tissue bed.

12. A method comprising:
  receiving a model of explanted tissue, wherein the model includes a marked portion of a surgical margin of the explanted tissue;
  receiving an image of a patient anatomy, wherein the patient anatomy includes a tissue bed from which the explanted tissue is removed; and
  marking, in the image, a region of the tissue bed that was proximate to the marked portion of the surgical margin prior to removal of the explanted tissue.

13. The method of claim 12 further comprising:
  providing an overlay of the model on the image in an arrangement; and
  providing a control to accept or reject the arrangement.

14. The method of claim 12 further comprising:
  providing an overlay of the model on the image; and
  providing a control to select between hiding and showing the overlay.

15. The method of claim 12 further comprising:
  determining, from the model, an arrangement of the explanted tissue within the tissue bed prior to removal.

16. The method of claim 15, wherein the determining of the arrangement of the explanted tissue is based on a feature from a group consisting of: a fiducial feature of the explanted tissue, a fiducial feature of the tissue bed, and a fiducial feature formed by removal of the explanted tissue from the tissue bed.

17. The method of claim 12, wherein the marked portion of the surgical margin in the model represents disease detected less than a threshold distance away from the marked portion.

18. The method of claim 12, wherein the image is of the patient anatomy prior to the removal of the explanted tissue from the tissue bed.

19. The method of claim 12, wherein the image is of the patient anatomy after the removal of the explanted tissue from the tissue bed.

20. The method of claim 12, wherein the marking utilizes an indicator from a group consisting of: a color, an outline, a flag, emphasis, and de-emphasis.

* * * * *